United States Patent [19]

Renshaw et al.

[11] Patent Number: 5,483,570
[45] Date of Patent: Jan. 9, 1996

[54] BEARINGS FOR X-RAY TUBES

[75] Inventors: Anthony A. Renshaw, Albany; Minyoung Lee, Schenectady, both of N.Y.

[73] Assignee: General Electric Company, Schenectady, N.Y.

[21] Appl. No.: 264,869

[22] Filed: Jun. 24, 1994

[51] Int. Cl.[6] .................................................. H01J 35/10
[52] U.S. Cl. ........................................... 378/132; 378/133
[58] Field of Search .................................. 378/132, 133, 378/121, 125, 127, 130, 131, 141, 144, 199, 200

[56] References Cited

U.S. PATENT DOCUMENTS

| | | |
|---|---|---|
| 2,293,527 | 8/1942 | Atlee . |
| 3,694,685 | 9/1972 | Houston . |
| 3,954,582 | 5/1976 | Hepp et al. . |
| 4,024,424 | 5/1977 | Eggelsmann et al. . |
| 4,141,603 | 2/1979 | Remmers et al. . |
| 4,210,371 | 7/1980 | Gerkema et al. . |
| 4,357,555 | 11/1982 | Gerkema et al. . |
| 4,413,356 | 11/1983 | Hartl . |
| 4,490,264 | 12/1984 | Gerkema et al. . |
| 4,562,587 | 12/1985 | Gerkema et al. . |
| 4,596,474 | 6/1986 | VanRoemburg . |
| 4,614,445 | 9/1986 | Gerkema et al. . |
| 4,641,332 | 2/1987 | Gerkema . |
| 4,644,577 | 2/1987 | Gerkema et al. . |
| 4,677,651 | 6/1987 | Hartl et al. . |
| 4,678,348 | 7/1987 | Tielemans et al. . |
| 5,068,885 | 11/1991 | Vetter . |
| 5,381,456 | 1/1995 | Vetter et al. ............................. 378/133 |

*Primary Examiner*—David P. Porta
*Attorney, Agent, or Firm*—R. Thomas Payne; James Magee, Jr.

[57] ABSTRACT

An improved x-ray system/tube comprising an enclosure having oil contained therein, an oil pump, for circulating oil within the system, at least one cooling structure operatively connected to the enclosure and the oil pump, for cooling the oil, an x-ray tube, operatively positioned inside the enclosure for generating and directing x-rays toward a target, the x-ray tube comprising: a glass envelope, a cathode, operatively positioned in the glass envelope, an anode assembly including a rotor and a stator, operatively positioned relative to the rotor, a target, operatively positioned relative to the cathode and operatively connected to the anode assembly, for directing x-rays out of the system, and bearing structure having opposing surfaces and lubricant means having debris therein, operatively connected to the anode assembly, for enabling the target to rotate at a high rate and at a low resistance, the bearing structure including means for capturing the debris such that bearing performance is maintained at or near the level of a bearing structure having no debris therein. The debris capturing means can be grooved, operatively positioned in the bearing structure, for preventing debris from moving to the interface point between the bearing surfaces. This can be accomplished by positioning various grooves in various types of bearing and by forming ridges in the grooves already in the bearing for capturing the debris.

14 Claims, 6 Drawing Sheets fig. 1a fig. 1b fig. 2 fig. 3 fig. 4a fig. 4b fig. 5a fig. 5b fig. 5c fig. 5d fig. 6a fig. 6b fig. 7

1

BEARINGS FOR X-RAY TUBES

BACKGROUND OF THE INVENTION

This invention relates generally to equipment for diagnostic and therapeutic radiology and methods of making the same and, more particularly, to liquid metal grooved bearings for x-ray tubes used in x-ray generating equipment, such as computerized axial tomography (C.A.T.) scanners and more particularly concerns a means for capturing debris, such as from liquid metal oxidation, mechanical wear, chemical corrosion etc., which can clog the bearing and diminish bearing performance.

Modern diagnostic x-ray procedures often require a rapid sequence of high energy exposures. These procedures rapidly increase the temperature of both the anode and the bearing assembly. When the tolerance temperatures of these systems are approached or exceeded, the x-ray tube may have its useful life shortened or may even fail outright. One way to limit anode temperature is to increase the size and/or the rotation speed of the anode. However, increasing the size or rotation speed of the anode increases the axial and radial loads on the bearing assembly, thereby reducing the life of the bearing.

X-ray tubes with rotary anodes require a bearing system to provide axial and radial support to the rotating anode during operations. Most x-ray tubes are produced with the bearing system comprised of two ball bearings having a soft metal coating as a lubricant. Another type of x-ray tube supports its rotor axially with a magnetic bearing and radially with a sleeve bearing using a layer of liquid metal as the lubricant. At least one of supporting surfaces of the sleeve bearing has helical grooves to improve retention of the liquid metal during anode rotation. The liquid metal lubricants used in these sleeve bearings are low melting point, low vapor pressure gallium alloys which wet and separate the opposing bearing faces without substantially attacking the bearing faces.

Yet another type of x-ray tube supports the rotor in both the axial and radial direction with sleeve bearings having helical grooves in a liquid metal lubricant. One other type of x-ray tube uses a magnetic bearing as the primary support mechanism for the rotor and a ball bearing system as a back-up support system for when the magnetic bearing is interrupted or switched off. This tube also uses a spiral grooved bearing lubricated with metal liquid lubricant between the rotor and a cooling tube located at the end of the rotating shaft. This sliding bearing serves primarily for dissipating the heat produced in the anode and at the same time serves as an electrical contact for supplying the high voltage potential.

Another type of bearing system commonly used in x-ray tubes comprises two ball bearings. Ball bearings used in x-ray tubes are typically lubricated with soft, solid metal coatings because the more conventional ball bearing lubricants are not suitable for use in the high vacuum operating environment of the x-ray tube. The solid metal coating type of lubricant does not adequately dampen the chattering noise of the ball bearings and is not durable when used at continuously high speeds and temperatures.

A quieter, more durable alternative to metal coated ball bearing systems is the so-called hydrodynamic or fluid-film bearing. Hydrodynamic bearings used in x-ray tubes typically comprise a pair of cooperating bearing surfaces with a low vapor pressure liquid metal lubricant disposed in a gap between the surfaces. The lubricant wets the bearing surfaces so as to completely fill the gap without allowing any contact between the surfaces, even under loaded conditions. At least one of the bearing surfaces may be provided with spiral grooves to enhance dynamic stability and load capacity. Hydrodynamic sliding bearings will not produce bearing chatter and have the potential for long life. Such a bearing requires a low melting point, liquid metal lubricant which wets the supporting bearing faces so that the gap between the supporting faces is completely filled by the lubricant without allowing any contact between the bearing surfaces even under loaded conditions. Furthermore, the liquid metal lubricant of these bearings functions well at dissipating heat produced in the anode and at the same time can serve as a contact for supplying the necessary high voltage potential.

However, at high operating speeds, instability can develop in the liquid lubricant which breaks up the liquid metal layer in a spiral groove bearing and limits the speed range of the bearing. One difficulty with liquid metal spiral groove bearings is that debris can clog the bearing. The debris evolves from a number of sources including liquid metal oxidation, mechanical wear, and chemical corrosion. If Mo is used for the bearing material, a reactive layer is always formed between the liquid metal and Mo. This layer can act as a precipitant, which can clog the bearing. When the bearing is clogged by this debris, its performance is substantially impaired in that the load capacity is diminished and the bearing causes the tube to experience power losses due to viscous drag increase.

Accordingly, there is a need for a hydrodynamic grooved bearing which can rotate at high speeds without debris impairing tube performance by diminishing load capacity or causing power losses due to increased viscous drag.

SUMMARY OF THE INVENTION

The above-mentioned needs are met by the present invention which is an x-ray system comprising an enclosure having oil contained therein, an oil pump, operatively positioned relative to the enclosure for circulating oil within the system, at least one cooling means, operatively connected to the enclosure and the oil pump, for cooling the oil, an x-ray tube, operatively positioned inside the enclosure, for generating and directing x-rays toward a target, the x-ray tube comprising: a glass envelope, a cathode, operatively positioned in the glass envelope, an anode assembly including a rotor and a stator, operatively positioned relative to the rotor, a target, operatively positioned relative to the cathode and operatively connected to the anode assembly, for directing x-rays out of the system, and bearing structure having opposing surfaces and lubricant means having debris therein, operatively connected to the anode assembly, for enabling the target to rotate at a high rate and at a low resistance, the bearing structure including means for capturing the debris such that bearing performance is maintained at or near the level of a bearing structure having no debris.

Another aspect of the present invention includes an x-ray system wherein the capturing means further comprises, a groove, operatively positioned in the bearing structure, for preventing debris from moving to the interface point between the bearing surfaces.

Still another aspect of the present invention is an x-ray tube comprising: a glass envelope, a cathode, operatively positioned in the glass envelope, an anode assembly including a rotor and a stator, operatively positioned relative to the rotor, a target, operatively positioned relative to the cathode and connected to the anode assembly, for directing x-rays out of the system, and bearing means including lubricant means having debris therein, operatively connected to the anode assembly, for enabling the target to rotate at a high rate and at a low resistance, the bearing means including debris capturing means for trapping debris such that bearing performance is maintained at or near the same level as bearing means having no debris therein.

Another aspect of the present invention includes an x-ray tube wherein the capturing means further comprises: at least one groove, operatively positioned in the bearing structure, for preventing debris from moving to the interface point between the bearing surfaces.

It is therefore and object of the present invention to provide an x-ray system and/or an x-ray tube having a means for capturing debris, such as from liquid metal oxidation, mechanical wear, chemical corrosion etc., which can clog the bearing and diminish bearing performance so that the bearing performs nearly as well as when no debris is present in the bearing.

Another object of the present invention is to provide a means to prevent or severely reduce the tendency of spiral grooved bearings to be clogged by debris thereby substantially impairing bearing performance.

Still another object of the present invention is to provide a means for capturing performance diminishing debris in x-ray bearings.

Yet another object of the present invention is to provide a bearing which can rotate at high speeds without debris impairing tube performance by diminishing load capacity or causing power losses due to increased viscous drag.

Other objects and advantages of the present invention will become apparent upon reading the following detailed description and the appended claims with reference to the accompanying drawings.

DESCRIPTION OF THE DRAWINGS

FIG. 1b is a sectional view with parts removed of the x-ray system of FIG. 1a;

DETAILED DESCRIPTION OF THE INVENTION

Figure 1A:
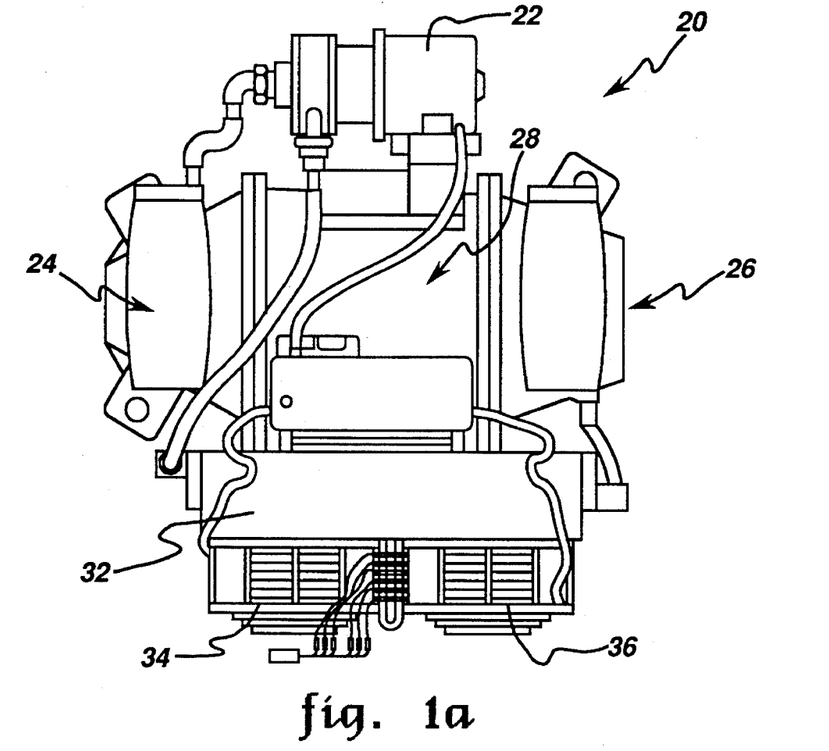
FIG. 1a is a plan view of a representative x-ray system.
Figure 1B:
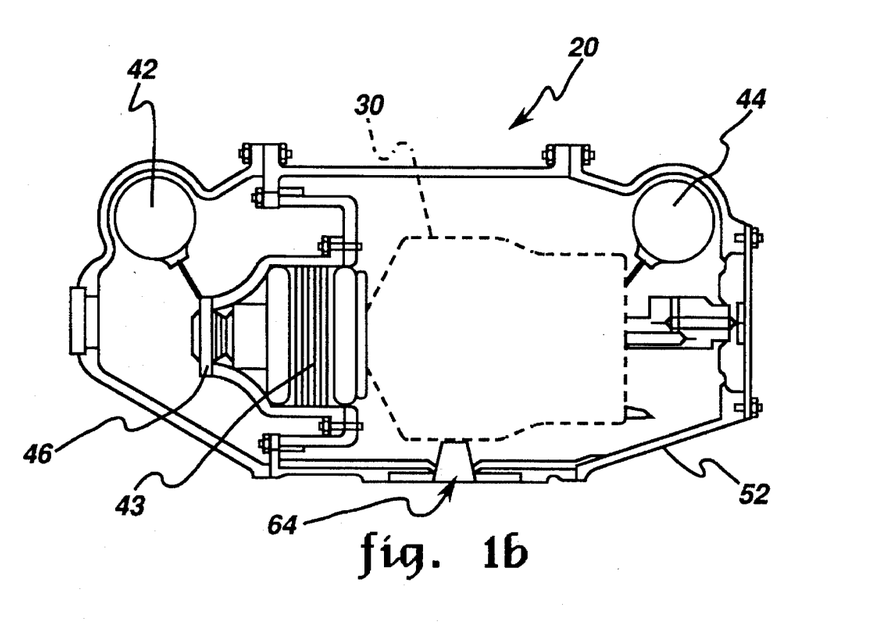
Figure 2:
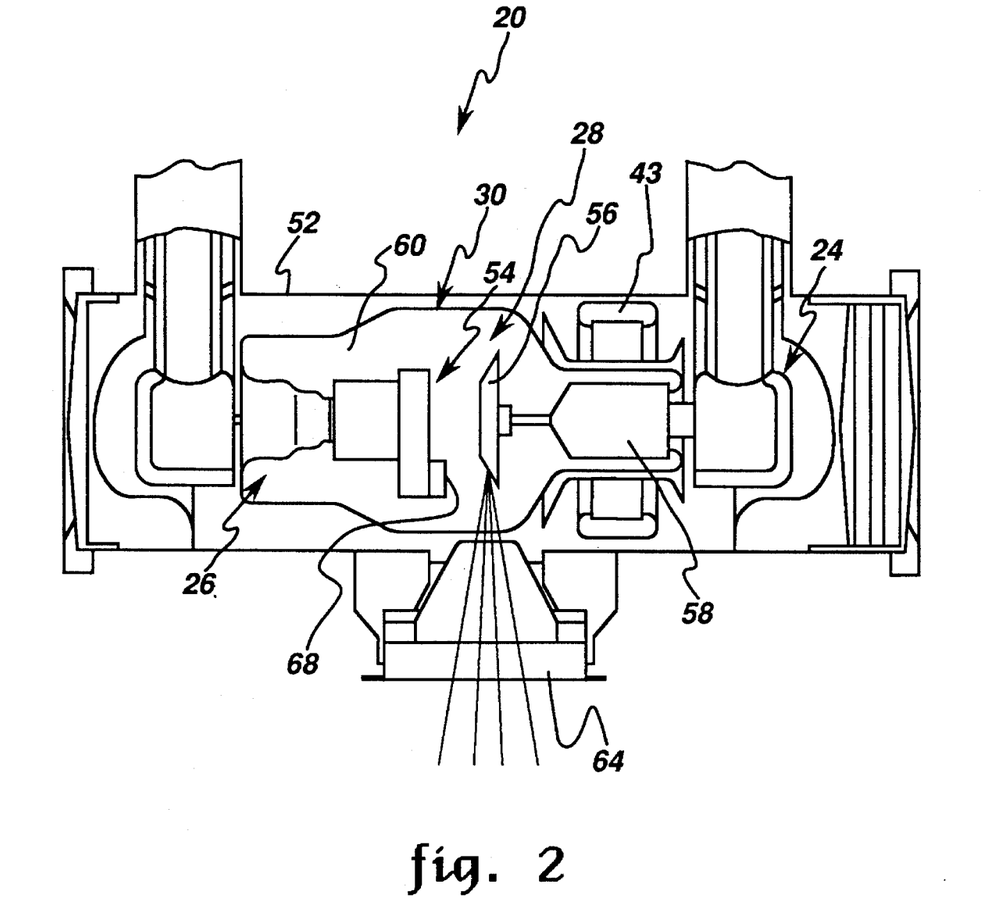
FIG. 2 is a schematic representation of another representative x-ray system having an x-ray tube positioned therein.

An x-ray system embodying the present invention in one preferred form thereof is illustrated as generally designated by the numeral 20 in FIGS. 1a, 1b and 2. As can be seen, the system 20 comprises an oil pump 22, an anode end 24, a cathode end 26, a center section 28 positioned between the anode end and the cathode end, which contains the x-ray tube 30. A radiator 32 for cooling the oil is positioned to one side of the center section and may have fans 34 and 36 operatively connected to the radiator 32 for providing cooling air flow over the radiator as the hot oil circulates therethrough. The oil pump 22 is provided for circulating the hot oil through the system 20 and through the radiator 32, etc. As shown in FIG. 1b, electrical connections are provided in the anode receptacle 42 and the cathode receptacle 44.

As shown in FIG. 2, the x-ray system 20 comprises a casing 52 preferably made of aluminum and lined with lead and a cathode plate 54, a rotating target disc 56 and a rotor 58 enclosed in a glass envelope 60. A stator 43 is positioned outside the glass envelope 60 inside the lead lined casing 52 relative to the rotor 58. The casing 52 is filled with oil for cooling and high voltage insulation purposes as was explained above. A window 64 for emitting x-rays is operatively formed in the casing 52 and relative to the target disc 56 for allowing generated x-rays to exit the x-ray system 20.

Figure 3:
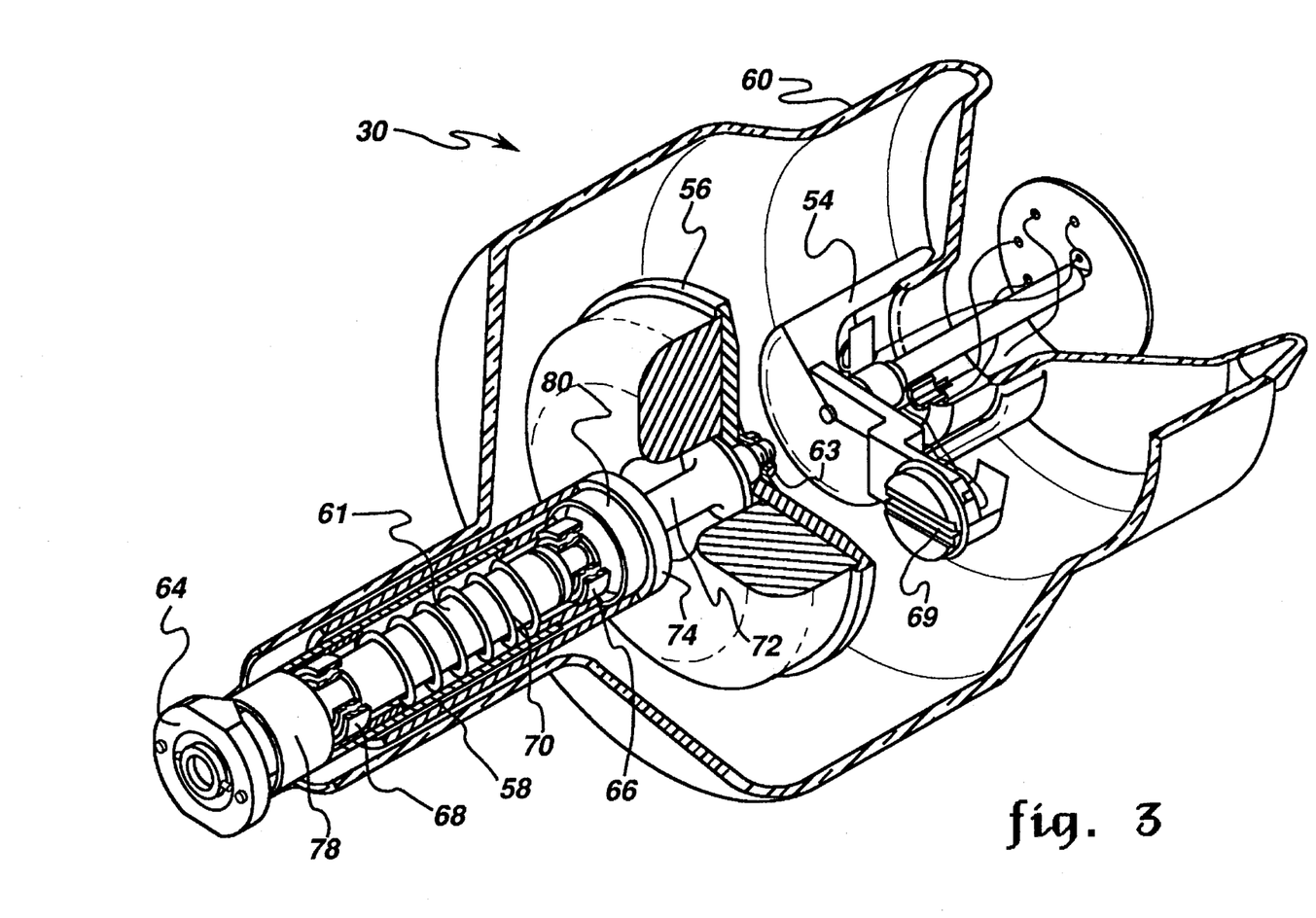
FIG. 3 is a partial perspective view of a representative x-ray tube with parts removed, parts in section, and parts broken away.

Referring to FIG. 3, there is shown a representative x-ray tube 30 having a cathode 54 positioned inside the glass envelope 60. As is well known, inside the glass envelope there is a vacuum of about $10^{-5}$ to about $10^{-9}$ torr. The electricity generates x-rays that are aimed from the cathode filament 68 to the anode target or the top of the target disc 56. The target disc is conventionally connected to a rotating shaft 61 at one end by a Belleville nut 63 and by another nut at the other end 64. A front bearing 66 and a rear bearing 68 are operatively positioned on the shaft 61 and are held in position in a conventional manner. The bearings 66 and 68 are usually silver lubricated and are susceptible to failure at high operating temperatures.

A preload spring 70 is positioned about the shaft 60 between the bearings 66, 68 for maintaining load on the bearings during expansion and contraction of the anode assembly. A rotor stud 72 is utilized to space the end of the rotor most proximate the target 56 from the rotor hub 74. The bearings, both front 66 and rear 68, are held in place by bearing retainers 78 and 80. The rotor assembly also includes a stem ring 82 and a stem 84 all of which help to provide for the rotation of the rotor 58 with the target 56.

The temperature in the area of the filament 69 can get as high as about 2500° C. Other temperatures include about 1100° C. near the center of the rotating target 56, which rotates at about 10,000 rpm. Temperatures of the focal spot on the target 56 can approximate 3200° C. and temperatures on the outside edge of the rotating target 56 approach about 1300° C. The temperature in the area of the rotor hub 74 approach 700° C. and of the front bearing 66 approaches 450° C. maximum. Obviously, as one moves from the target 56 to the rotor 58 and stator 43, the temperature appears to decrease. It has recently been found that temperatures on the surface of the rotor 58 can approach up to 700° C.

During operation of some x-ray systems, severe protocol users have maximized usage of the system by making as many scans at high peak power in as short a time as possible. One of the problems with utilizing any x-ray system in this continuous type of operation is the amount of heat that is generated, which may in fact destroy the silver bearings 66, 68, especially the front bearing 66.

If the x-ray tube target 56 and rotor 58 were allowed to continue to rotate at 10,000 rpm between scans, the bearings would wear out prematurely and cause the tube to fail. Thus, if it appears that there would to be more than 60 seconds between scans, the x-ray system operating control system software is programmed to brake the rotor by rapidly slowing it completely down to zero (0) rpm. However, when ready to initiate a scan, the control system software is programmed to return the target and the rotor to 10,000 rpm as quickly as possible. These rapid accelerations and brakes are utilized because, among other reasons, there are a number of resonant frequencies that must be avoided during the acceleration from zero (0) to 10,000 rpm and the brake from 10,000 rpm to zero (0) rpm. In order to pass through these resonant frequencies both immediately before a scan or a series of scans and after a scan or series of scans as fast as possible, the x-ray system applies maximum power to bring the target, or anode, to 10,000 rpm or down to zero (0) rpm in the least amount of time possible.

It should be noted that the x-ray tube target and rotor can be accelerated to 10,000 rpm from a dead stop in about 12 to about 15 seconds and slowed down at about the same rate. Vibration from the resonant frequencies is a real problem, if the tube is allowed to spin to a stop without braking.

In order to prevent or severely reduce the tendency of spiral grooved bearings to be clogged by debris thereby substantially impairing bearing performance, means for capturing debris as part of the bearings normal operation itself without impairing bearing performance has been designed. This debris capturing means or trap can take the form of an extra groove at the center of the bearing which may or may not have additional surface features to improve debris entrapment.

A spiral groove bearing capable of supporting both radial and axial loads is made of materials which can withstand gallium or gallium alloys as the lubricating fluid. There materials would be W, Mo, Re, or alloys thereof. Both the radial (or journal) and axial bearings have chevron-shaped grooves machined in the surface to improve the loading and stability of the bearing.

Figure 4A:
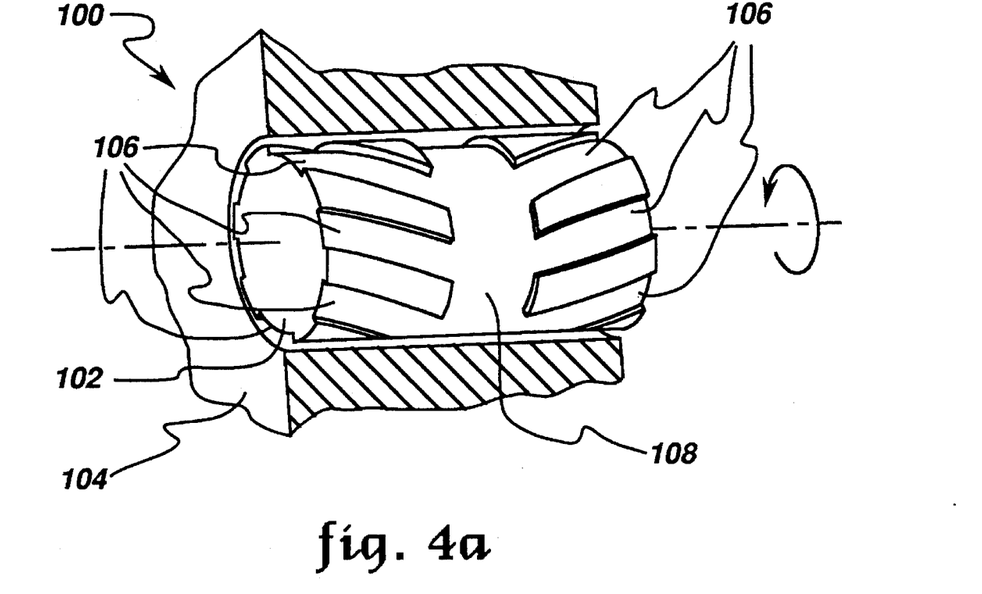
FIG. 4a is a schematic view of a typical prior art radial spiral groove bearing.

As best seen in FIG. 4a, a typical radial (or journal) spiral grooved bearing 100 used to support radial loads is illustrated. The bearing 100 comprises a center shaft 102 and a mating piece 104 which fits closely over the shaft. Either the center shaft 102 or the mating piece 104 can have grooves 106 machined therein, although usually it is easier and preferred to machine the center shaft 102, as shown in FIG. 4a. Either the shaft 102 or the mating surface 104 can rotate as long as the relative motion therebetween pumps the lubricant to the center 108 of the bearing 100.

As illustrated in FIG. 4a, the grooves 106 are machined in the shaft 102 surface in such a manner that when the debris (not shown) is in the bearing, it is pumped to the center of the bearing where it clogs the groove 106 and increases wear on the mating surfaces 102, 104.

Figure 4B:
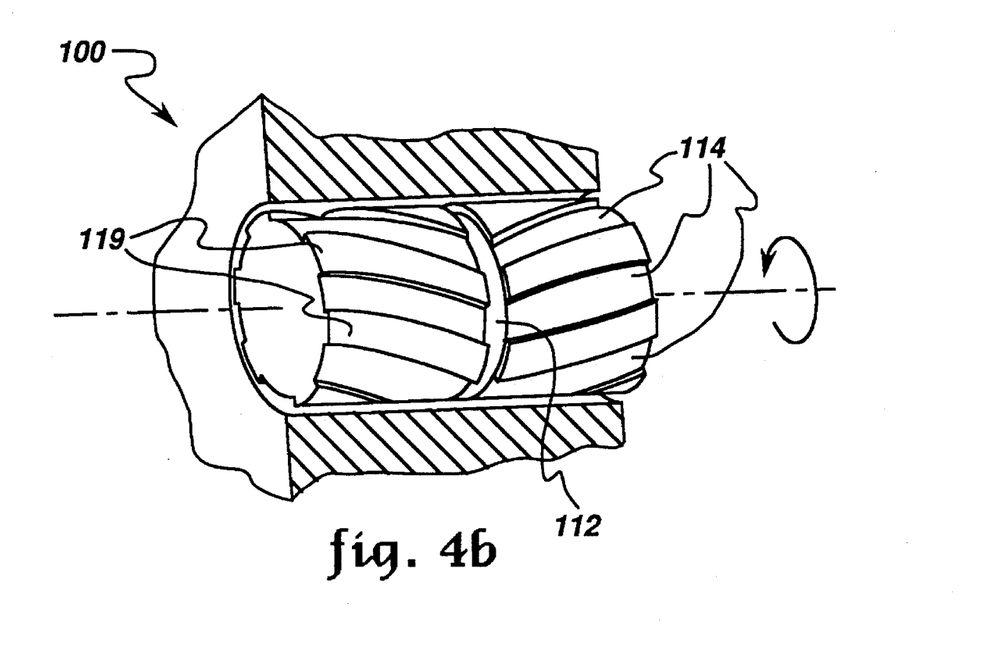
FIG. 4b is a schematic view of the bearing of FIG. 4a having a debris capturing means as used in the present invention.

FIG. 4b shows a bearing 110 similar to the bearing 100. However, it should be noted that the bearing 110 has an additional groove or trap 112 in the center of the bearing which serves as the debris capturing means or trap. When debris is present in bearing 110, the debris is pumped to the center of the bearing and circulates about the bearing. The depth of the this groove or trap 112 is important so that the circumferential pressure is not entirely short-circuited, which would decrease the bearing load capacity. Typical depths for the trap 112 are about 5 to about 50% of the depth of the chevron grooves in the rest of the bearing. The depth should be as small as possible while still achieving the above performance parameters. A trap with a depth of 50% or more of the other chevron grooves would still function, although at a reduced load capacity. A surface pattern similar to those illustrated in FIGS. 5b–d could also be used to entrap the debris and to ensure that the pressure is not short circuited.

Figure 5A:
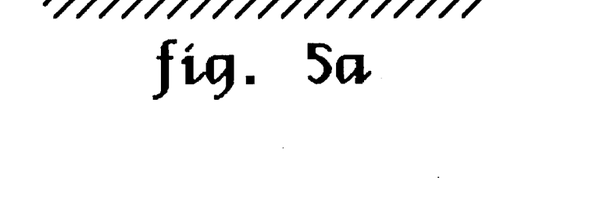
FIG. 5a illustrates the normal groove/bearing surface profile as used in the prior art.
Figure 5B:
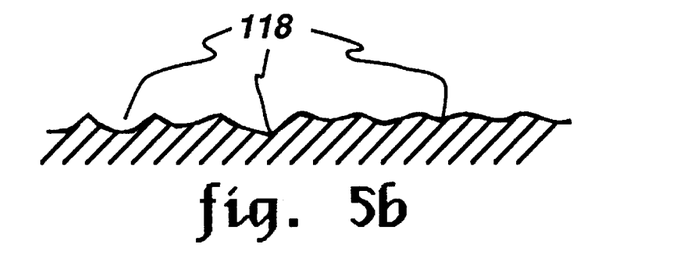
FIGS. 5b–5d illustrates three of the possible plurality of groove surface profiles that could be formed in the bearing surface to capture debris as used in the present invention.
Figure 5C:
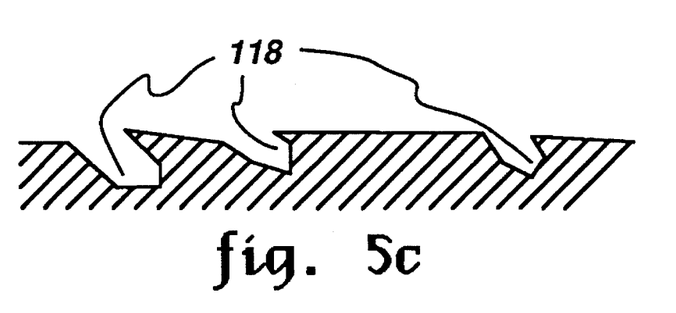
Figure 5D:
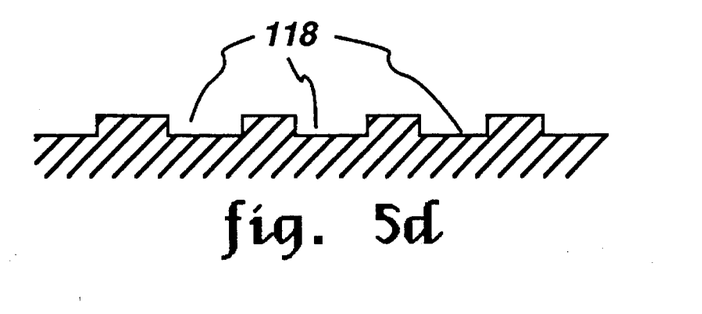

As shown in FIG. 5b–d, a few illustrative surface profiles of a means for capturing debris or trap are illustrated. In each of these figures, the arrows indicate the length along the groove. FIG. 5a clearly illustrates the normal smooth surface of the groove. FIGS. 5b, 5c, and 5d illustrate various holes or ridges machined or otherwise placed in the surface of the trap 112 or the spiral groove bearing ridges 114 for capturing the debris. An alternative would be to form the holes or ridges 114 in the bearing surface 119. It should be noted that the height of the holes or ridges 118 of the debris trap must be less than those of the bearing surface 119 in FIG. 4b.

Figures 6A, 6B, 7:
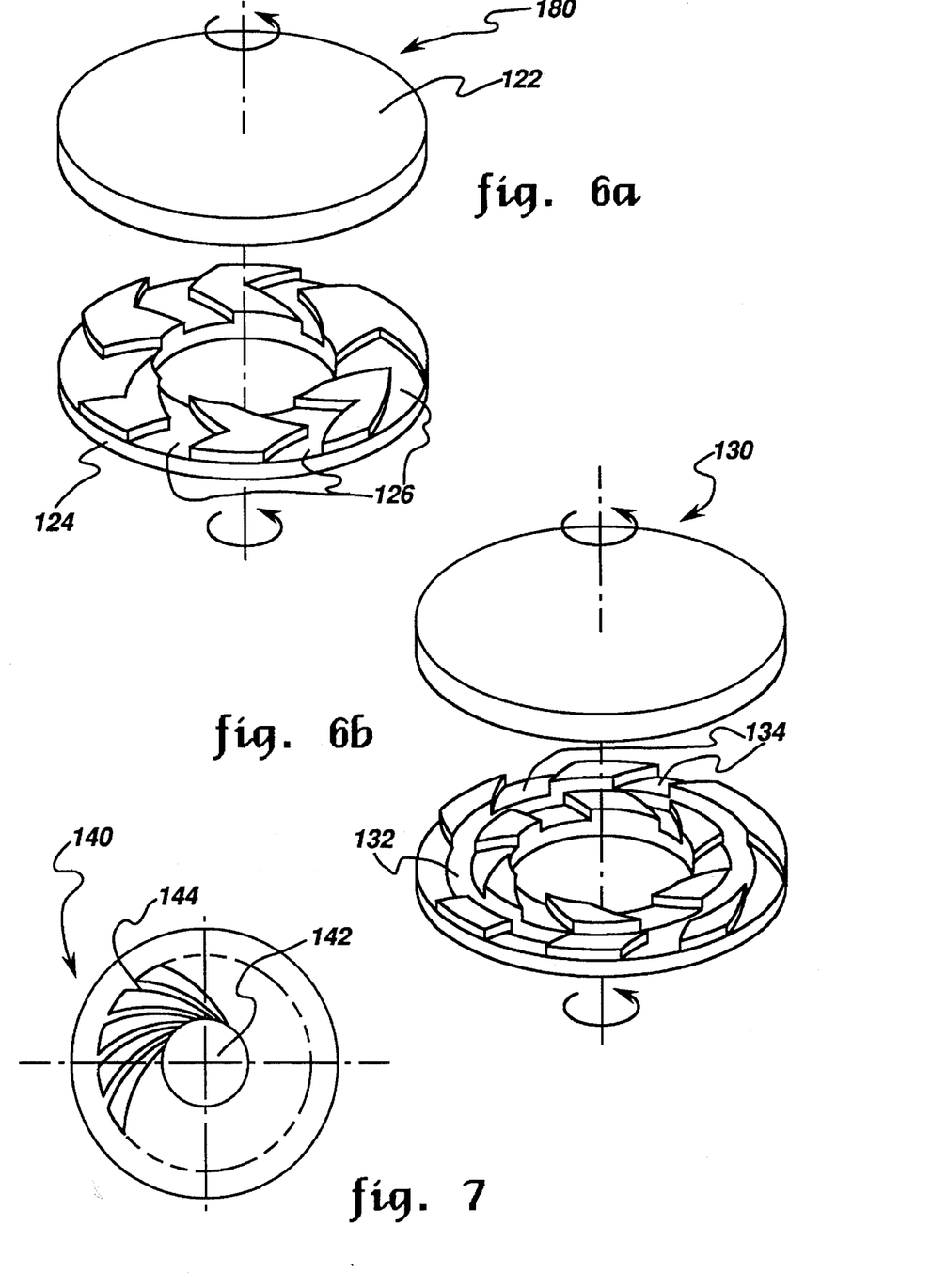
FIG. 6a is a schematic view of a typical prior art spiral groove.
FIG. 6b is a schematic view of the bearing of FIG. 6a having a debris capturing means as used in the present invention.
FIG. 7 is a schematic view of a pump-in thrust bearing as used in the present invention.

FIG. 6a illustrates a typical thrust spiral groove bearing used to support axial loads. This bearing 120 typically comprises two plates, one plate 122 with a smooth surface and one plate 124 has spiral grooves 126 machined therein. As before, either plate 122, 124 can rotate so long as the relative motion of the plate pumps the lubricant to the center or apex of the grooves 126.

When debris is in the bearing 120, it is pumped by the grooves 126 to the apex where it clogs the grooves. Debris can also result in wear at the apex diameter where the debris is caught by the groove apex and makes contact with the opposite side of flat surface 122.

FIG. 6b illustrates a thrust bearing 130 having an additional circumferential groove 132 at the apex radius. When debris is in the bearing 130, it is pumped circumferentially into groove 132 and does not interfere or degrade the load capacity of the bearing or increase viscous losses. The depth of the groove may be the same as the chevron grooves 134 or it may be many time greater or even less. Specifically, the depth of the groove is essentially immaterial other than it must be sufficient to capture and prevent any debris from migrating to the bearing interface. In bearing 130, the additional groove or trap does not degrade the bearing performance with respect to load capacity.

FIG. 7 illustrates an alternative thrust bearing 140 design which pumps lubricant and debris to the center of the bearing. The capturing means or trap 142 is formed in the center of the bearing 140 by means such as machining. With reference again to FIG. 5, debris can be further entrapped by each groove 144 if the surface of the groove is further operated on to have holes or ridges 118 for catching debris, as discussed earlier.

Experiments have been conducted to measure the load capacity and viscous power loss in a thrust spiral groove bearing with substantial gallium oxidation and no capturing means or trap mechanism. Measured power losses were about four times higher and the forces are somewhat lower (approximately 80%) than analytically predicted. It is believed a major cause of this discrepancy in bearing performance is the clogging action of gallium oxide and other debris.

The foregoing has described a means for capturing performance diminishing debris in x-ray bearings. While specific embodiments of the present invention have been described, it will be apparent to those skilled in the art that various modifications thereto can be made without departing from the spirit and scope of the invention as defined in the appended claims.

What is claimed is:

1. An x-ray system comprising;

an enclosure;

at least one cooling means, operatively connected to the enclosure, for cooling the system;

an x-ray tube, operatively positioned inside the enclosure, for generating and directing x-rays toward a target, the x-ray tube comprising:

an envelope;

a cathode, operatively positioned in the envelope;

an anode assembly including a rotor and a stator, operatively positioned relative to the rotor;

a target, operatively positioned relative to the cathode and operatively connected to the anode assembly, for directing x-rays out of the system; and bearing structure having opposing surfaces and lubricant means having debris therein, operatively connected to the anode assembly, for enabling the target to rotate at a high rate and at a low resistance, the bearing structure including at least one groove, operatively positioned in the bearing structure, for preventing debris from moving to the interface point between the bearing surfaces wherein the depth of the groove is selected so that the circumferential pressure in the bearing does not decrease the bearing load capacity and wherein at least one ridge is placed in at least one of the bearing grooves such that the height of the ridges for trapping the debris must be less than those of the bearing structure.

2. The x-ray tube of claim 1, wherein the debris capturing means comprises a depression operatively positioned in the center of the bearing so that the lubricant contained in the bearing is pumped circumferentially into the depression and does not interfere or degrade the load capacity of the bearing or increase viscous losses.

3. The x-ray tube of claim 1, wherein the at least one groove is operatively formed in the bearing so that when debris is in the bearing, the debris is pumped to the center of the bearing and circulates about the bearing.

4. The x-ray tube of claim 3, wherein the depth of the groove is selected so that the circumferential pressure in the bearing does not decrease the bearing load capacity.

5. The x-ray tube of claim 4, wherein the depth of the bearing groove is from about 5 µm to about 25 µm.

6. The x-ray tube of claim 4, wherein the depth of the bearing groove is about 5 µm.

7. The x-ray tube of claim 5, wherein the at least one groove is formed at the apex radius of the bearing so that the lubricant is pumped circumferentially into the groove and does not interfere or degrade the load capacity of the bearing or increase viscous losses.

8. An x-ray tube comprising:

an envelope;

a cathode, operatively positioned in the envelope;

an anode assembly including a rotor and a stator, operatively positioned relative to the rotor;

a target, operatively positioned relative to the cathode and connected to the anode assembly, for directing x-rays out of the system; and bearing means having debris therein, operatively connected to the anode assembly, for enabling the target to rotate at a high rate and at a low resistance, the bearing means including at least one groove, operatively positioned in the bearing structure, for preventing debris from moving to the interface point between the bearing surfaces and wherein ridges are placed in each of the at least one bearing grooves such that the height of the ridges for trapping the debris must be less than those of the bearing means such that bearing performance is maintained at or near the same level as bearing means having no debris therein.

9. The x-ray tube of claim 8, wherein the debris capturing means comprises a depression operatively positioned in the center of the bearing so that the lubricant contained in the bearing is pumped circumferentially into the groove and does not interfere or degrade the load capacity of the bearing or increase viscous losses.

10. The x-ray tube of claim 8, wherein the groove, operatively formed in the bearing so that when debris is in the bearing, the debris is pumped to the center of the bearing and circulates about the bearing.

11. The x-ray tube of claim 10, wherein the depth of the groove is selected so that the circumferential pressure in the bearing does not decrease the bearing load capacity.

12. The x-ray tube of claim 11, wherein the depth of the bearing groove is from about 5 µm to about 25 µm.

13. The x-ray tube of claim 11, wherein the depth of the bearing groove is about 5 µm.

14. The x-ray tube of claim 12, wherein the groove is formed at the apex radius of the bearing so that the lubricant is pumped circumferentially into the groove and does not interfere or degrade the load capacity of the bearing or increase viscous losses.

* * * * *